(12) United States Patent
Safai et al.

(10) Patent No.: US 10,495,611 B1
(45) Date of Patent: Dec. 3, 2019

(54) APPARATUS, SYSTEM, AND METHOD FOR NON-DESTRUCTIVE TESTING

(71) Applicant: The Boeing Company, Chicago, IL (US)

(72) Inventors: Morteza Safai, Newcastle, WA (US); Kimberly D. Meredith, Newcastle, WA (US)

(*) Notice: Subject to any disclaimer, the term of this patent is extended or adjusted under 35 U.S.C. 154(b) by 0 days.

(21) Appl. No.: 16/209,734

(22) Filed: Dec. 4, 2018

(51) Int. Cl.
*G01B 9/02* (2006.01)
*G01N 29/24* (2006.01)
*B64F 5/60* (2017.01)
*G01B 11/30* (2006.01)
*G01N 21/17* (2006.01)

(52) U.S. Cl.
CPC ........... *G01N 29/2418* (2013.01); *B64F 5/60* (2017.01); *G01B 9/02031* (2013.01); *G01B 11/30* (2013.01); *G01N 21/1702* (2013.01); *G01N 2021/1706* (2013.01)

(58) Field of Classification Search
CPC ............ G01B 9/02015; G01B 9/02017; G01B 9/02019; G01B 9/02027; G01B 9/02049
See application file for complete search history.

(56) References Cited

U.S. PATENT DOCUMENTS

| 6,833,554 | B2 | 12/2004 | Wooh | |
| 10,078,049 | B2 * | 9/2018 | Safai | G01N 21/45 |
| 2006/0201253 | A1 | 9/2006 | Gonzales et al. | |
| 2014/0293285 | A1 | 10/2014 | Prieto et al. | |
| 2017/0336324 | A1 * | 11/2017 | Safai | G01N 21/45 |

* cited by examiner

*Primary Examiner* — Jonathan M Hansen

(57) ABSTRACT

Disclosed herein is an apparatus. The apparatus comprises a beam guide comprising an input aperture, a cavity, and a plurality of output apertures. The input aperture is coupled with the cavity and configured to receive a laser beam and to direct the laser beam into the cavity. The plurality of output apertures is formed in the cavity and spaced apart along the cavity, wherein each output aperture of the plurality of output apertures is configured to direct a portion of the laser beam out of the cavity. The apparatus comprises a plurality of fiber optic lines coupled to the beam guide and configured to receive ultrasonic information corresponding to portions of the laser beam that have exited the cavity through the plurality of output apertures.

20 Claims, 4 Drawing Sheets

APPARATUS, SYSTEM, AND METHOD FOR NON-DESTRUCTIVE TESTING

FIELD

This disclosure relates generally to testing structures, and more particularly to non-destructive testing of parts using interferometry.

BACKGROUND

Non-destructive testing may be used to test parts. By using non-destructive testing, properties of a material of the part may be analyzed without causing damage to the material. Certain non-destructive testing is performed using interferometry. Interferometry uses superposition to combine waves from a single source to provide information. In some instances, interferometry uses a laser light directed toward a surface area of an object. The laser light may take different paths before returning to a detector. The detector may determine a result relating to the surface area of the object. The result may be analyzed to determine whether there is a defect in the object.

Generally, multiple laser beams may be used with multiple interferometers. However, multiple laser beams, from different sources, may lead to inaccurate results.

SUMMARY

The subject matter of the present application has been developed in response to the present state of the art, and in particular, in response to the shortcomings of conventional interferometry techniques, that have not yet been fully solved by currently available techniques. Accordingly, the subject matter of the present application has been developed to provide an apparatus, system, and associated method that overcome at least some of the above-discussed shortcomings of prior art techniques.

Disclosed herein is an apparatus. The apparatus comprises a beam guide comprising an input aperture, a cavity, and a plurality of output apertures. The input aperture is coupled with the cavity and configured to receive a laser beam and to direct the laser beam into the cavity. The plurality of output apertures is formed in the cavity and spaced apart along the cavity, wherein each output aperture of the plurality of output apertures is configured to direct a portion of the laser beam out of the cavity. The apparatus comprises a plurality of fiber optic lines coupled to the beam guide and configured to receive ultrasonic information corresponding to portions of the laser beam that have exited the cavity through the plurality of output apertures. The preceding subject matter of this paragraph characterizes example 1 of the present disclosure.

Each output aperture of the plurality of output apertures is configured to direct the portion of the laser beam out of the cavity such that each portion of the laser beam directed out of a respective one of the plurality of output apertures has a substantially similar intensity. The preceding subject matter of this paragraph characterizes example 2 of the present disclosure, wherein example 2 also includes the subject matter according to example 1, above.

The substantially similar intensity comprises being within ten percent of other intensities of the plurality of output apertures. The preceding subject matter of this paragraph characterizes example 3 of the present disclosure, wherein example 3 also includes the subject matter according to example 2, above.

At least one output aperture of the plurality of output apertures comprises a partially reflective material. The preceding subject matter of this paragraph characterizes example 4 of the present disclosure, wherein example 4 also includes the subject matter according to any one of examples 1-3, above.

A first portion of the laser beam is directed through the partially reflective material and a second portion of the laser beam is reflected by the partially reflective material. The preceding subject matter of this paragraph characterizes example 5 of the present disclosure, wherein example 5 also includes the subject matter according to example 4, above.

Each of the plurality of output apertures comprises a material. The material of at least one of the output apertures of the plurality of output apertures is different from that of at least another of the output apertures of the plurality of output apertures. The preceding subject matter of this paragraph characterizes example 6 of the present disclosure, wherein example 6 also includes the subject matter according to any one of examples 1-5, above.

A first output aperture of the plurality of output apertures comprises a partially reflective material through which a first portion of the laser beam is directed out of the cavity and a second portion of the laser beam is reflected. A last output aperture of the plurality of output apertures comprises a non-reflective material through which a remaining portion of the laser beam is directed out of the cavity. The first portion of the laser beam and the remaining portion of the laser beam comprise substantially similar intensities. The preceding subject matter of this paragraph characterizes example 7 of the present disclosure, wherein example 7 also includes the subject matter according to any one of examples 1-6, above.

A first output aperture of the plurality of output apertures comprises a first partially reflective material that directs a first portion of the laser beam out of the cavity. A second output aperture of the plurality of output apertures comprises a second partially reflective material that directs a second portion of the laser beam out of the cavity. The first and second partially reflective materials comprise different reflective properties, and the first portion of the laser beam and the second portion of the laser beam comprise substantially similar intensities. The preceding subject matter of this paragraph characterizes example 8 of the present disclosure, wherein example 8 also includes the subject matter according to any one of examples 1-7, above.

The first portion of the laser beam is directed out of the cavity before the second portion of the laser beam is directed out of the cavity. The first portion of the laser beam comprises a first percentage of the laser beam. A remaining portion of the laser beam remains in the cavity after the first portion of the laser beam is directed out of the cavity. The second portion of the laser beam comprises a second percentage of the remaining portion of the laser beam. The second percentage is greater than the first percentage. The preceding subject matter of this paragraph characterizes example 9 of the present disclosure, wherein example 9 also includes the subject matter according to example 8, above.

The plurality of fiber optic lines is disposed at least partially within the beam guide. The preceding subject matter of this paragraph characterizes example 10 of the present disclosure, wherein example 10 also includes the subject matter according to any one of example 1-9, above.

The plurality of fiber optic lines is configured to receive the ultrasonic information corresponding to portions of the laser beam that have exited the cavity through the plurality of output apertures, and the ultrasonic information is directed toward the beam guide. The preceding subject matter of this paragraph characterizes example 11 of the present disclosure, wherein example 11 also includes the subject matter according to any one of examples 1-10, above.

The cavity comprises a first side and a second side, opposite the first side. The input aperture is disposed on the first side of the cavity. The plurality of output apertures is disposed on the second side of the cavity. The preceding subject matter of this paragraph characterizes example 12 of the present disclosure, wherein example 12 also includes the subject matter according to any one of examples 1-11, above.

An interior surface of the first side of the cavity comprises a reflective coating. The preceding subject matter of this paragraph characterizes example 13 of the present disclosure, wherein example 13 also includes the subject matter according to example 12, above.

An interior surface of the second side of the cavity comprises a partially reflective material having an opacity that varies from a first opacity to a second opacity, the first opacity being greater than the second opacity. The preceding subject matter of this paragraph characterizes example 14 of the present disclosure, wherein example 14 also includes the subject matter according to example 12, above.

Further disclosed herein is a system. The system includes a laser, selectively operable to generate a laser beam. The system includes an apparatus. The apparatus includes a beam guide comprising an input aperture, a cavity, and a plurality of output apertures. The input aperture is coupled with the cavity and configured to receive the laser beam and to direct the laser beam into the cavity. The plurality of output apertures is formed in the cavity and spaced apart along the cavity, wherein each output aperture of the plurality of output apertures is configured to direct a portion of the laser beam out of the cavity. The apparatus includes a plurality of fiber optic lines coupled to the beam guide and configured to receive ultrasonic information corresponding to portions of the laser beam that have exited the cavity through the plurality of output apertures. The system includes a meter coupled to the plurality of fiber optic lines and configured to generate data corresponding to the ultrasonic information received by the plurality of fiber optic lines. The preceding subject matter of this paragraph characterizes example 15 of the present disclosure.

The system comprises a processing device configured to receive the data and produce an image corresponding to the data. The preceding subject matter of this paragraph characterizes example 16 of the present disclosure, wherein example 16 also includes the subject matter according to example 15, above.

The image comprises a two-dimensional mapping of a surface of an object, a three-dimensional mapping of the surface of the object, or a combination thereof. The preceding subject matter of this paragraph characterizes example 17 of the present disclosure, wherein example 17 also includes the subject matter according to example 16, above.

The meter comprises an interferometer. The preceding subject matter of this paragraph characterizes example 18 of the present disclosure, wherein example 18 also includes the subject matter according to any one of examples 15-17, above.

Additionally disclosed herein is a method of non-destructive testing of an object. The method comprises illuminating the object using an apparatus. The apparatus comprises a beam guide comprising an input aperture, a cavity, and a plurality of output apertures. The input aperture is coupled with the cavity and configured to receive a laser beam and to direct the laser beam into the cavity. The plurality of output apertures is formed in the cavity and spaced apart along the cavity. Each output aperture of the plurality of output apertures is configured to direct a portion of the laser beam out of the cavity. The apparatus comprises a plurality of fiber optic lines coupled to the beam guide and configured to receive ultrasonic information corresponding to portions of the laser beam that have exited the cavity through the plurality of output apertures. The method comprises generating data corresponding to the ultrasonic information received by the plurality of fiber optic lines. The method comprises forming a mapping of a surface of the object using the data. The method comprises analyzing the mapping of the surface of the object to determine whether the object has a defect. The preceding subject matter of this paragraph characterizes example 19 of the present disclosure.

The mapping comprises a two-dimensional mapping or a three-dimensional mapping. The preceding subject matter of this paragraph characterizes example 20 of the present disclosure, wherein example 19 also includes the subject matter according to example 19, above.

The described features, structures, advantages, and/or characteristics of the subject matter of the present disclosure may be combined in any suitable manner in one or more examples and/or implementations. In the following description, numerous specific details are provided to impart a thorough understanding of examples of the subject matter of the present disclosure. One skilled in the relevant art will recognize that the subject matter of the present disclosure may be practiced without one or more of the specific features, details, components, materials, and/or methods of a particular example or implementation. In other instances, additional features and advantages may be recognized in certain examples and/or implementations that may not be present in all examples or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific examples that are illustrated in the appended drawings. Understanding that these drawings depict only typical examples of the subject matter and are not therefore to be considered to be limiting of its scope, the subject matter will be described and explained with additional specificity and detail through the use of the drawings, in which.

DETAILED DESCRIPTION

Reference throughout this specification to "one example," "an example," or similar language means that a particular feature, structure, or characteristic described in connection with the example is included in at least one example of the present disclosure. Appearances of the phrases "in one example," "in an example," and similar language throughout this specification may, but do not necessarily, all refer to the same example. Similarly, the use of the term "implementation" means an implementation having a particular feature, structure, or characteristic described in connection with one or more examples of the present disclosure, however, absent an express correlation to indicate otherwise, an implementation may be associated with one or more examples.

Figure 1:
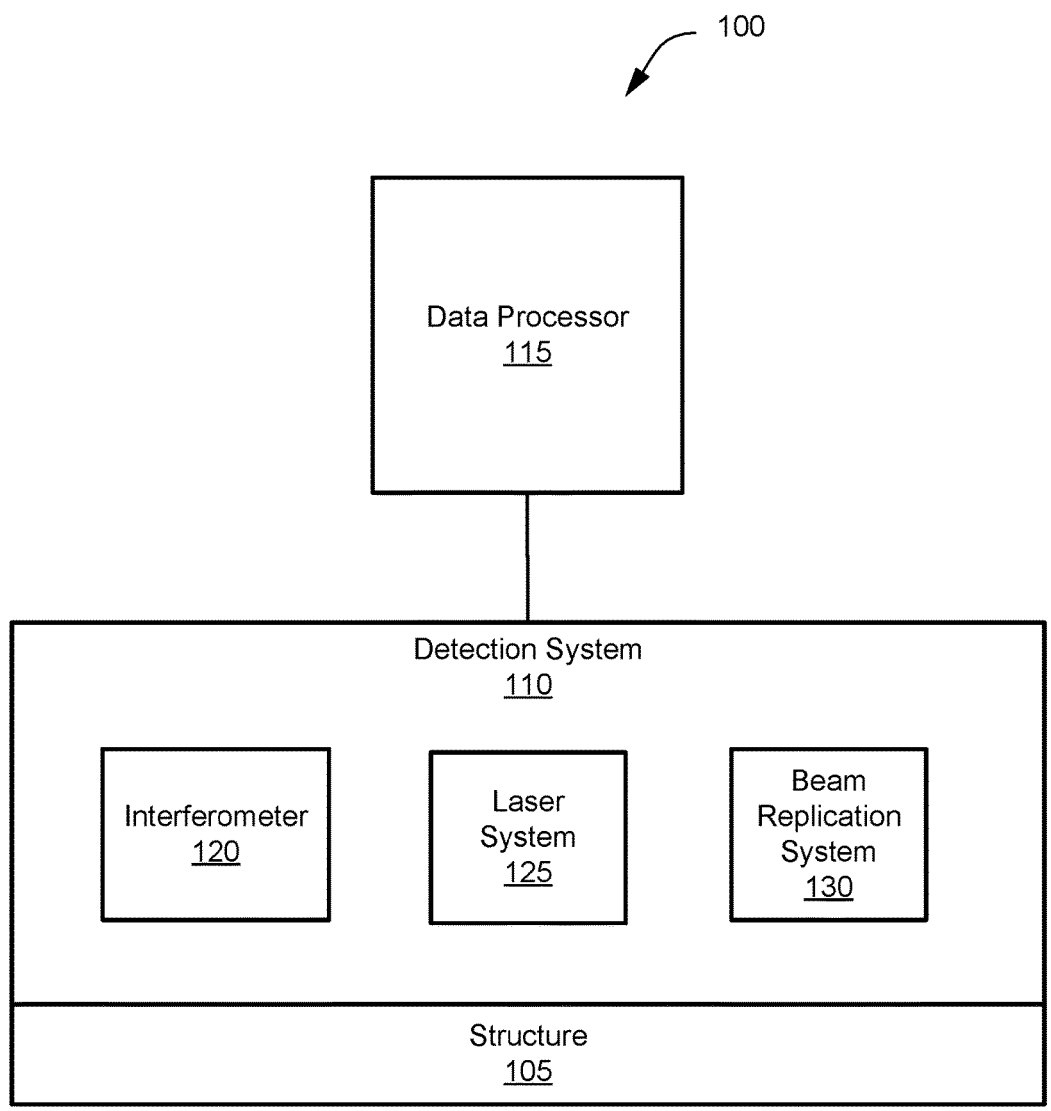
FIG. 1 is a schematic block diagram of a system for performing interferometry non-destructive testing, according to one or more examples of the present disclosure.

As shown in FIG. 1, and according to some examples, a system 100 for performing interferometry non-destructive testing on a structure 105, is illustrated. The structure 105 may be any suitable structure, such as a portion of an aircraft (e.g., wing, fuselage, etc.), or another manufactured structure. The system 100 includes a detection system 110 used to capture information corresponding to the structure 105 and a data processor 115 that processes the information captured by the detection system 110. The data processor 115 may be any suitable information handling device capable of processing the captured information. In one example, the data processor 115 is a computer, a smart phone, a processing device, or the like. In one example, the data processor 115 includes one or more processors for processing the captured information and a display for showing a mapping of the surface of the structure 105 produced from the captured information. The data processor 115 receives captured information (e.g., data) and produces an image corresponding to the data. In an example, the data processor 115 produces a two-dimensional mapping of a surface of an object and/or a three-dimensional mapping of the surface of the object.

As used herein, the structure 105 (e.g., an object) has a defect if there is a deformation on the surface of the structure 105, such as a deformation resulting from air trapped under the surface of the structure 105. In some situations, the air trapped under the surface of the structure 105 result from disbonded materials (e.g., lack of bonding between materials) under the surface of the structure 105. The system 100 is configured to be used to detect the defect in the structure 105.

The detection system 110 includes an interferometer 120, a laser system 125, and a beam replication system 130. The interferometer 120 is a meter used to capture information (e.g., ultrasonic information) related to the structure 105 and may be any suitable type of interferometer. The interferometer 120 is used to detect multiple laser produced interferometry points. Moreover, the laser system 125 is selectively operable to generate a laser beam directed toward the structure 105 so ultrasonic information created by the laser beam may be captured by the interferometer 120 thereby capturing information corresponding to the structure 105. As described herein, multiple interferometry points are captured using a single laser beam. The laser system 125 may include any suitable laser excitation source capable of being selectively operated to generate a laser beam, such as a gas laser, a chemical laser, a dye laser, a solid-state laser, a semiconductor laser, and so forth. The laser system 125 includes an ultrasonic testing delivery head, for delivering the laser beam, in some examples. The beam replication system 130 is used to receive a laser beam from the laser system 125, divide the laser beam, and output portions of the laser beam that each have a substantially similar intensity, as explained in greater detail in FIG. 3.

Figure 2:
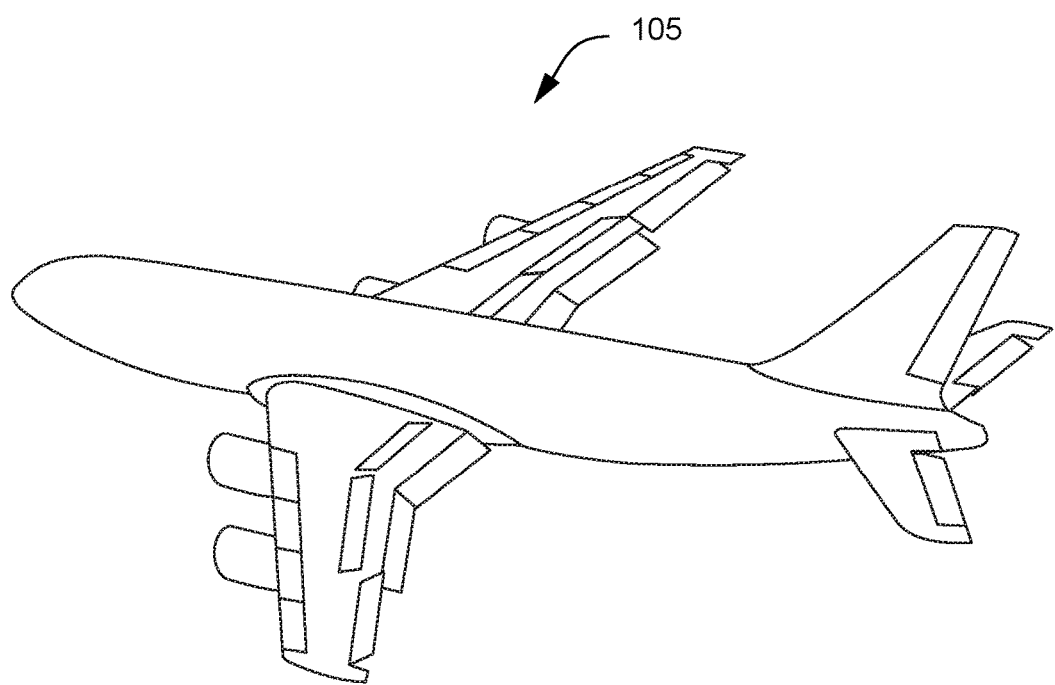
FIG. 2 is a perspective view of a structure on which interferometry non-destructive testing may be performed, according to one or more examples of the present disclosure.

Referring to FIG. 2, and according to one example, the structure 105 on which non-destructive testing is performed is an airplane, or the structure 105 is any suitable manufactured device such as vehicles, aircraft, turbines, engines, and equipment operable in space like environments (e.g., satellite, rockets, missiles, space stations, space vehicles, space simulators). In certain examples, the structure 105 is tested using non-destructive testing. In such examples, the beam replication system 130 is used to divide a single input laser beam to enable multiple interferometer measurements based on the same laser beam. According to some examples, the beam replication system 130 includes a cavity, an input aperture coupled with the cavity and configured to receive a laser beam and to direct the laser beam into the cavity, and multiple output apertures formed in the cavity and spaced apart along the cavity. Each output aperture of the multiple output apertures is configured to direct a portion of the laser beam out of the cavity such that each portion of the laser beam directed out of a respective one of the multiple output apertures has a substantially similar intensity.

Figure 3:
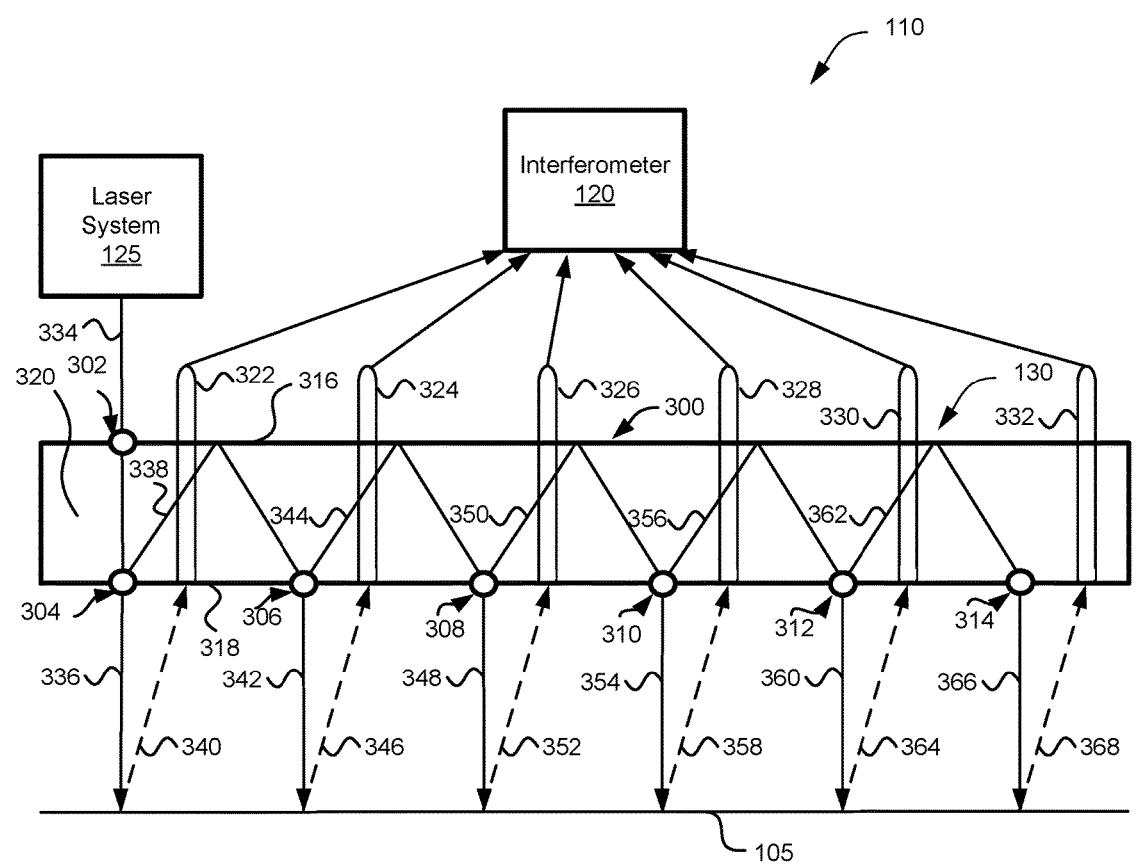
FIG. 3 is a schematic block diagram of an example of a detection system, according to one or more examples of the present disclosure.

Referring to FIG. 3, one example of a schematic block diagram of the detection system 110 is illustrated. As part of the detection system 110, the beam replication system 130 includes a planar shaped laser beam guide 300. It should be noted that while the laser beam guide 300 is substantially planar, in other implementations, the laser beam guide 300 may be shaped differently. The laser beam guide 300 may be enclosed or partially enclosed.

The laser beam guide 300 includes an input aperture 302 and output apertures 304, 306, 308, 310, 312, 314. Although six output apertures 304, 306, 308, 310, 312, 314 are illustrated, any number of output apertures greater than one may be part of the laser beam guide 300. The input aperture 302 and/or the output apertures 304, 306, 308, 310, 312, 314 includes one or more of an aperture, an opening, a coating, and a material to facilitate a laser beam entering the laser beam guide 300 through the input aperture 302 and the laser beam exiting the laser beam guide 300 through one or more of the output apertures 304, 306, 308, 310, 312, 314. In some examples, each of the output apertures 304, 306, 308, 310, 312, 314 includes the material, which is situated within the corresponding apertures. The material of at least one of the output apertures 304, 306, 308, 310, 312, 314 may be different from that of at least another of the output apertures 304, 306, 308, 310, 312, 314. By having different materials among output apertures 304, 306, 308, 310, 312, 314, the output apertures 304, 306, 308, 310, 312, 314 each output a different proportion of the laser beam that contacts the output apertures 304, 306, 308, 310, 312, 314. The material may be any suitable material, such as a partially reflective material or a non-reflective material.

The input aperture 302 is positioned on a first side 316 of the laser beam guide 300 and the output apertures 304, 306, 308, 310, 312, 314 are positioned on a second side 318 of the laser beam guide 300. In some implementations, the first side 316 of the laser beam guide 300 includes a reflective material or coating that reflects a laser beam. The first side 316 of the laser beam guide 300 and the second side 318 of the laser beam guide 300 enclose a cavity 320 through which the laser beam passes. As used herein, the first side 316 of the laser beam guide 300 is considered a first side of the cavity 320, and the second side 318 of the laser beam guide 300 is considered a second side of the cavity 320.

The input aperture 302 is coupled with the cavity 320, receives a laser beam, and directs the laser beam into the cavity 320. Moreover, the output apertures 304, 306, 308, 310, 312, 314 are formed in the cavity 320 and spaced apart along the cavity 320. In some implementations, the output apertures 304, 306, 308, 310, 312, 314 are spaced apart from an adjacent output aperture by a substantially equal distance. The substantially equal distance is a distance that varies by less than 1, 2, 5, 10, or 15 percent in some examples.

The laser beam guide 300 includes fiber optic lines 322, 324, 326, 328, 330, 332. Although six fiber optic lines 322, 324, 326, 328, 330, 332 are illustrated, any number of fiber optic lines greater than one may be part of the laser beam guide 300. Each of the fiber optic lines 322, 324, 326, 328, 330, 332 is coupled to the laser beam guide 300. In certain examples, each of the fiber optic lines 322, 324, 326, 328, 330, 332 is disposed at least partially, or entirely, within the cavity 320 of the laser beam guide 300 and is configured to receive a reflected laser beam. In various examples, the fiber optic lines 322, 324, 326, 328, 330, 332 may be attached to an exterior of the laser beam guide 300 and/or disposed adjacent to the laser beam guide 300. The fiber optic lines 322, 324, 326, 328, 330, 332 are configured to receive ultrasonic information and to provide the ultrasonic information to the interferometer 120 for analysis and/or multiplexing. In other words, the fiber optic lines 322, 324, 326, 328, 330, 332 are configured to receive ultrasonic information corresponding to portions of a single laser beam that exit the cavity 320 through the output apertures 304, 306, 308, 310, 312, 314, and the ultrasonic information is directed toward the laser beam guide 300. The fiber optic lines 322, 324, 326, 328, 330, 332 may be any suitable type of device capable of capturing the ultrasonic information and directing the ultrasonic information to the interferometer 120. Although only one interferometer 120 is illustrated, in other examples, the interferometer 120 includes multiple interferometers to handle the multiple fiber optic lines 322, 324, 326, 328, 330, 332 concurrently. The interferometer 120 is coupled to the multiple fiber optic lines 322, 324, 326, 328, 330, 332 and configured to generate data corresponding to the ultrasonic information received by the multiple fiber optic lines 322, 324, 326, 328, 330, 332.

During operation, the laser system 125 directs a laser beam 334 through the input aperture 302 into the cavity 320. The laser beam 334 travels through the cavity 320 and contacts the output aperture 304. The output aperture 304 directs a first portion 336 of the laser beam 334 out of the cavity 320 and reflects a second portion 338 of the laser beam 334 into the cavity 320. The output aperture 304 may include a partially reflective material that directs the first portion 336 of the laser beam 334 out of the cavity 320 and reflects the second portion 338 of the laser beam 334 into the cavity 320. In some implementations, the first portion 336 of the laser beam 334 may be approximately 17 percent (e.g., ⅙) of the laser beam 334, and the second portion 338 of the laser beam 334 may be approximately 83 percent (e.g., ⅚) of the laser beam 334. Although various percentages are used herein to describe a proportion of a laser beam, these percentages are for example purposes only, and in various examples may be any suitable percentage. Moreover, the second portion 338 of the laser beam 334 may be considered the remaining portion of the laser beam 334 that remains in the cavity 320. As illustrated, the first portion 336 of the laser beam 334 produces ultrasound corresponding to the structure 105 resulting in first ultrasonic information 340 being directed into the fiber optic line 322 toward the interferometer 120.

The second portion 338 of the laser beam 334 reflects off of the first side 316 of the laser beam guide 300 and contacts the output aperture 306. The output aperture 306 directs a third portion 342 of the laser beam 334 out of the cavity 320 and reflects a fourth portion 344 of the laser beam 334 into the cavity 320. In some examples, the output aperture 306 includes a partially reflective material that directs the third portion 342 of the laser beam 334 out of the cavity 320 and reflects the fourth portion 344 of the laser beam 334 into the cavity 320. In some implementations, the third portion 342 of the laser beam 334 is approximately 20 percent (e.g., ⅕) of the second portion 338 of the laser beam 334, and the fourth portion 344 of the laser beam 334 is approximately 80 percent (e.g., ⅘) of the second portion 338 of the laser beam 334. Accordingly, in some implementations, the third portion 342 of the laser beam 334 is approximately the same percentage of the original laser beam 334 as the first portion 336 of the laser beam 334. Therefore, the first portion 336 of the laser beam 334 and the third portion 342 of the laser beam 334 have substantially similar intensity, energy, and/or power in certain examples. As used herein, having a substantially similar intensity, energy, and/or power means that the intensity, energy, and/or power may be within 1, 2, 5, or 10 percent of one another. Moreover, in some examples, the fourth portion 344 of the laser beam 334 is considered the remaining portion of the laser beam 334 that remains in the cavity 320. As illustrated, the third portion 342 of the laser beam 334 produces ultrasound corresponding to the structure 105 resulting in second ultrasonic information 346 being directed into the fiber optic line 324 toward the interferometer 120.

The fourth portion 344 of the laser beam 334 reflects off of the first side 316 of the laser beam guide 300 and contacts the output aperture 308. The output aperture 308 directs a fifth portion 348 of the laser beam 334 out of the cavity 320 and reflects a sixth portion 350 of the laser beam 334 into the cavity 320. The output aperture 308 may include a partially reflective material that directs the fifth portion 348 of the laser beam 334 out of the cavity 320 and reflects the sixth portion 350 of the laser beam 334 into the cavity 320. In some implementations, the fifth portion 348 of the laser beam 334 is approximately 25 percent (e.g., ¼) of the fourth portion 344 of the laser beam 334, and the sixth portion 350 of the laser beam 334 is approximately 75 percent (e.g., ¾) of the fourth portion 344 of the laser beam 334. Accordingly, in some implementations, the fifth portion 348 of the laser beam 334 is approximately the same percentage of the original laser beam 334 as the first and third portions 336, 342 of the laser beam 334. Therefore, the first portion 336 of the laser beam 334, the third portion 342 of the laser beam 334, and the fifth portion 348 of the laser beam 334 may have substantially similar intensity, energy, and/or power. Moreover, the sixth portion 350 of the laser beam 334 may be considered the remaining portion of the laser beam 334 that remains in the cavity 320. As illustrated, the fifth portion 348 of the laser beam 334 produces ultrasound corresponding to the structure 105 resulting in third ultrasonic information 352 being directed into the fiber optic line 326 toward the interferometer 120.

The sixth portion 350 of the laser beam 334 reflects off of the first side 316 of the laser beam guide 300 and contacts the output aperture 310. The output aperture 310 directs a seventh portion 354 of the laser beam 334 out of the cavity 320 and reflects an eighth portion 356 of the laser beam 334 into the cavity 320. The output aperture 310 may include a partially reflective material that directs the seventh portion 354 of the laser beam 334 out of the cavity 320 and reflects the eighth portion 356 of the laser beam 334 into the cavity 320. In some implementations, the seventh portion 354 of the laser beam 334 is approximately 33 percent (e.g., ⅓) of the sixth portion 350 of the laser beam 334, and the eighth portion 356 of the laser beam 334 is approximately 67 percent (e.g., ⅔) of the sixth portion 350 of the laser beam 334. Accordingly, in some implementations, the seventh portion 354 of the laser beam 334 is approximately the same percentage of the original laser beam 334 as the first, third, and fifth portions 336, 342, 348 of the laser beam 334. Therefore, the first portion 336 of the laser beam 334, the third portion 342 of the laser beam 334, the fifth portion 348 of the laser beam 334, and the seventh portion 354 of the laser beam 334 may have substantially similar intensity, energy, and/or power. Moreover, the eighth portion 356 of the laser beam 334 may be considered the remaining portion of the laser beam 334 that remains in the cavity 320. As illustrated, the seventh portion 354 of the laser beam 334 produces ultrasound corresponding to the structure 105 resulting in fourth ultrasonic information 358 being directed into the fiber optic line 328 toward the interferometer 120.

The eighth portion 356 of the laser beam 334 reflects off of the first side 316 of the laser beam guide 300 and contacts the output aperture 312. The output aperture 312 directs a ninth portion 360 of the laser beam 334 out of the cavity 320 and reflects a tenth portion 362 of the laser beam 334 into the cavity 320. The output aperture 312 may include a partially reflective material that directs the ninth portion 360 of the laser beam 334 out of the cavity 320 and reflects the tenth portion 362 of the laser beam 334 into the cavity 320. In some implementations, the ninth portion 360 of the laser beam 334 is approximately 50 percent (e.g., ½) of the eighth portion 356 of the laser beam 334, and the tenth portion 362 of the laser beam 334 is approximately 50 percent (e.g., ½) of the eighth portion 356 of the laser beam 334. Accordingly, the ninth portion 360 of the laser beam 334 may be approximately the same percentage of the original laser beam 334 as the first, third, fifth, and seventh portions 336, 342, 348, 354 of the laser beam 334. Therefore, the first portion 336 of the laser beam 334, the third portion 342 of the laser beam 334, the fifth portion 348 of the laser beam 334, the seventh portion 354 of the laser beam 334, and the ninth portion 360 of the laser beam 334 may have substantially similar intensity, energy, and/or power. Moreover, the tenth portion 362 of the laser beam 334 may be considered the remaining portion of the laser beam 334 that remains in the cavity 320. As illustrated, the ninth portion 360 of the laser beam 334 produces ultrasound corresponding to the structure 105 resulting in fifth ultrasonic information 364 being directed into the fiber optic line 330 toward the interferometer 120.

The tenth portion 362 of the laser beam 334 reflects off of the first side 316 of the laser beam guide 300 and contacts the output aperture 314. The output aperture 314 directs an eleventh portion 366 of the laser beam 334 out of the cavity 320. The output aperture 314 may include a non-reflective material that directs the eleventh portion 366 of the laser beam 334 out of the cavity 320. In some implementations, the eleventh portion 366 of the laser beam 334 is approximately 100 percent of the tenth portion 362 of the laser beam 334. Accordingly, in some implementations, the eleventh portion 366 of the laser beam 334 is approximately the same percentage of the original laser beam 334 as the first, third, fifth, seventh, and ninth portions 336, 342, 348, 354, 360 of the laser beam 334. Therefore, the first portion 336 of the laser beam 334, the third portion 342 of the laser beam 334, the fifth portion 348 of the laser beam 334, the seventh portion 354 of the laser beam 334, the ninth portion 360 of the laser beam 334, and the eleventh portion 366 of the laser beam 334 may have substantially similar intensity, energy, and/or power. In various implementations, the first portion 336 of the laser beam 334, the third portion 342 of the laser beam 334, the fifth portion 348 of the laser beam 334, the seventh portion 354 of the laser beam 334, the ninth portion 360 of the laser beam 334, and the eleventh portion 366 of the laser beam 334 may have a substantially similar phase (e.g., may be in phase with one another). As used herein, a substantially similar phase may mean that phases are within 1, 2, 5, or 10 degrees of one another. As illustrated, the eleventh portion 366 of the laser beam 334 produces ultrasound corresponding to the structure 105 resulting in sixth ultrasonic information 368 being directed into the fiber optic line 332 toward the interferometer 120.

Accordingly, each of the output apertures 304, 306, 308, 310, 312, 314 directs a portion of the laser beam 334 out of the cavity 320 such that each portion of the laser beam directed out of a respective one of the output apertures 304, 306, 308, 310, 312, 314 has a substantially similar intensity, energy, and/or power.

It should be noted that the partially reflective materials of the output apertures 304, 306, 308, 310, 312 may have different reflective properties to result in directing (e.g., allowing to pass) different percentages of the laser beam 334 through the output apertures 304, 306, 308, 310, 312. In one example, the output aperture 304 includes a partially reflective material that is more opaque than the partially reflective material of the output aperture 306. In another example, the output aperture 306 includes a partially reflective material that is more opaque than the partially reflective material of the output aperture 308. In a further example, the output aperture 308 includes a partially reflective material that is more opaque than the partially reflective material of the output aperture 310. In an additional example, the output aperture 310 includes a partially reflective material that is more opaque than the partially reflective material of the output aperture 312. As used herein, opaque refers to not being transparent, or blocking a portion of a laser beam from passing through a material. For example, if a first material is more opaque than a second material, the first material blocks a greater percentage of a laser beam from passing therethrough. Moreover, as used herein, opacity refers to how opaque a material is. For example, a material that has a higher opacity is more opaque than a material with a lower opacity. The opacity of a material of the output apertures 304, 306, 308, 310, 312, 314 through which the laser beam passes may vary such that the output apertures 304, 306, 308, 310, 312, 314 are ordered in descending opacity from highest opacity (e.g., output aperture 304) to lowest opacity (e.g., output aperture 314). The lowest opacity may block a low percentage, or no percentage, of a laser beam from passing therethrough.

Figure 4:
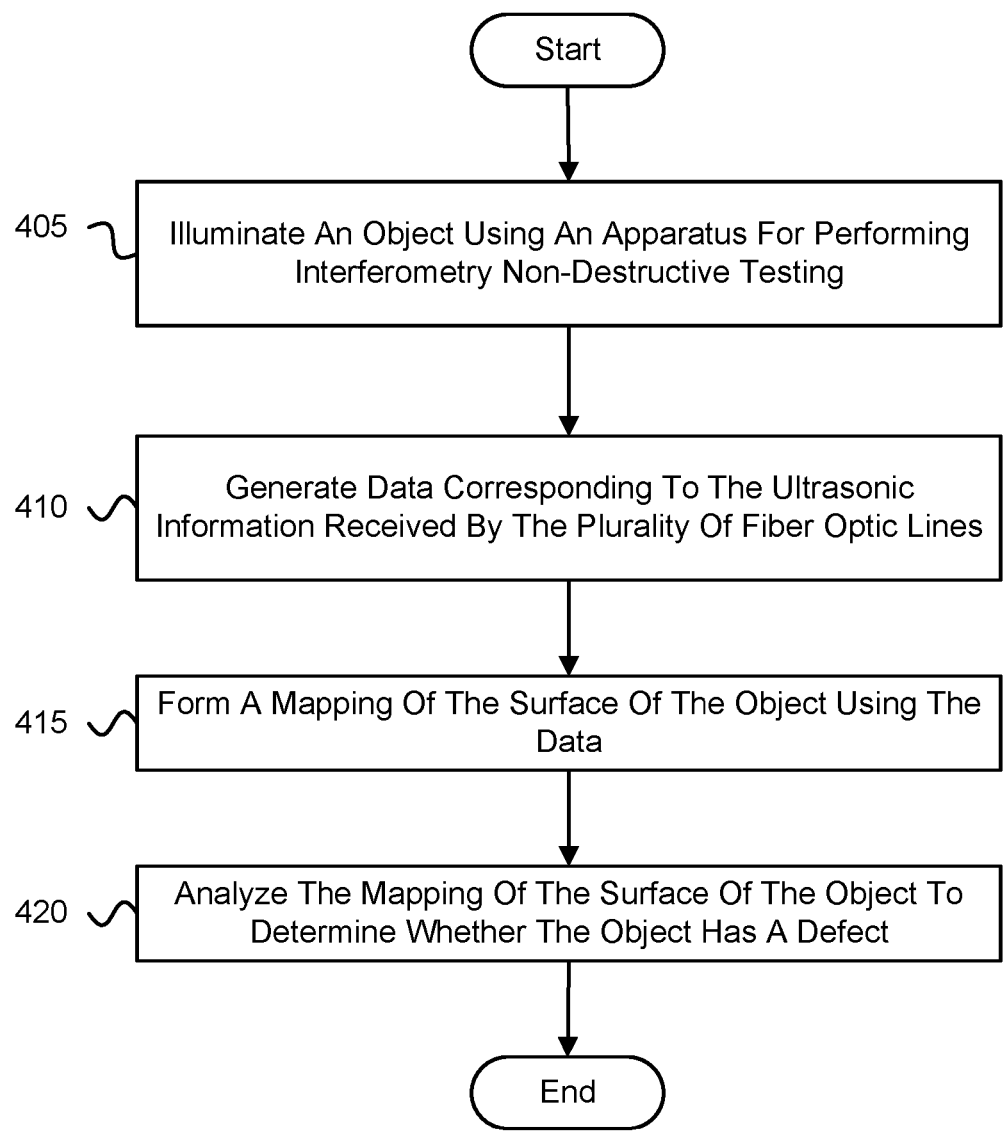
FIG. 4 is a schematic flow diagram of a method of non-destructive testing of an object, according to one or more examples of the present disclosure.

Referring to FIG. 4, one example of a method 400 of non-destructive testing of an object is shown. The method 400 includes illuminating the object using an apparatus (e.g., the detection system 110) at 405. The apparatus includes a beam guide. The beam guide includes an input aperture, a cavity, and a plurality of output apertures. The input aperture is coupled with the cavity and configured to receive a laser beam and to direct the laser beam into the cavity. The plurality of output apertures is formed in the cavity and spaced apart along the cavity. Each output aperture of the plurality of output apertures is configured to direct a portion of the laser beam out of the cavity. The apparatus includes a plurality of fiber optic lines coupled to the beam guide and configured to receive ultrasonic information corresponding to portions of the laser beam that have exited the cavity through the plurality of output apertures.

Additionally, the method 400 includes generating data corresponding to the ultrasonic information received by the plurality of fiber optic lines at 410. The data may be generated using the interferometer 120 and/or the data processor 115. Then, the method 400 may include forming a mapping of a surface of the object using the data at 415. The mapping of the surface of the object may be formed using the data by the data processor 115. The method 400 also includes analyzing the mapping of the surface of the object to determine whether the object has a defect at 420. In various examples, the data processor 115 may analyze the mapping of the surface of the object to determine whether the object has a defect.

In some implementations, the mapping includes a two-dimensional mapping and/or a three-dimensional mapping.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two." Moreover, unless otherwise noted, as defined herein a plurality of particular features does not necessarily mean every particular feature of an entire set or class of the particular features.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The schematic flow chart diagrams included herein are generally set forth as logical flow chart diagrams. As such, the depicted order and labeled steps are indicative of one example of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present subject matter may be embodied in other specific forms without departing from its spirit or essential characteristics. The described examples are to be considered in all respects only as illustrative and not restrictive. All changes which come within the meaning and range of equivalency of the claims are to be embraced within their scope.

What is claimed is:

1. An apparatus, comprising:
    a beam guide comprising an input aperture, a cavity, and a plurality of output apertures, wherein:
        the input aperture is coupled with the cavity and configured to receive a laser beam and to direct the laser beam into the cavity; and
        the plurality of output apertures is formed in the cavity and spaced apart along the cavity, wherein each output aperture of the plurality of output apertures is configured to direct a portion of the laser beam out of the cavity; and a plurality of fiber optic lines coupled to the beam guide and configured to receive ultrasonic information corresponding to portions of the laser beam that have exited the cavity through the plurality of output apertures.

2. The apparatus of claim 1, wherein each output aperture of the plurality of output apertures is configured to direct the portion of the laser beam out of the cavity such that each portion of the laser beam directed out of a respective one of the plurality of output apertures has a substantially similar intensity.

3. The apparatus of claim 2, wherein the substantially similar intensity comprises being within ten percent of other intensities of the plurality of output apertures.

4. The apparatus of claim 1, wherein at least one output aperture of the plurality of output apertures comprises a partially reflective material.

5. The apparatus of claim 4, wherein a first portion of the laser beam is directed through the partially reflective material and a second portion of the laser beam is reflected by the partially reflective material.

6. The apparatus of claim 1, wherein:
each of the plurality of output apertures comprises a material; and
the material of at least one of the output apertures of the plurality of output apertures is different from that of at least another of the output apertures of the plurality of output apertures.

7. The apparatus of claim 1, wherein:
a first output aperture of the plurality of output apertures comprises a partially reflective material through which a first portion of the laser beam is directed out of the cavity and a second portion of the laser beam is reflected;
a last output aperture of the plurality of output apertures comprises a non-reflective material through which a remaining portion of the laser beam is directed out of the cavity; and
the first portion of the laser beam and the remaining portion of the laser beam comprise substantially similar intensities.

8. The apparatus of claim 1, wherein:
a first output aperture of the plurality of output apertures comprises a first partially reflective material that directs a first portion of the laser beam out of the cavity;
a second output aperture of the plurality of output apertures comprises a second partially reflective material that directs a second portion of the laser beam out of the cavity; and
the first and second partially reflective materials comprise different reflective properties, and the first portion of the laser beam and the second portion of the laser beam comprise substantially similar intensities.

9. The apparatus of claim 8, wherein:
the first portion of the laser beam is directed out of the cavity before the second portion of the laser beam is directed out of the cavity;
the first portion of the laser beam comprises a first percentage of the laser beam;
a remaining portion of the laser beam remains in the cavity after the first portion of the laser beam is directed out of the cavity;
the second portion of the laser beam comprises a second percentage of the remaining portion of the laser beam; and
the second percentage is greater than the first percentage.

10. The apparatus of claim 1, wherein the plurality of fiber optic lines is disposed at least partially within the beam guide.

11. The apparatus of claim 1, wherein the plurality of fiber optic lines is configured to receive the ultrasonic information corresponding to portions of the laser beam that have exited the cavity through the plurality of output apertures, and the ultrasonic information is directed toward the beam guide.

12. The apparatus of claim 1, wherein:
the cavity comprises a first side and a second side, opposite the first side;
the input aperture is disposed on the first side of the cavity; and
the plurality of output apertures is disposed on the second side of the cavity.

13. The apparatus of claim 12, wherein an interior surface of the first side of the cavity comprises a reflective coating.

14. The apparatus of claim 12, wherein an interior surface of the second side of the cavity comprises a partially reflective material having an opacity that varies from a first opacity to a second opacity, the first opacity being greater than the second opacity.

15. A system, comprising:
a laser, selectively operable to generate a laser beam;
an apparatus, comprising:
a beam guide comprising an input aperture, a cavity, and a plurality of output apertures, wherein:
the input aperture is coupled with the cavity and configured to receive the laser beam and to direct the laser beam into the cavity; and
the plurality of output apertures is formed in the cavity and spaced apart along the cavity, wherein each output aperture of the plurality of output apertures is configured to direct a portion of the laser beam out of the cavity; and
a plurality of fiber optic lines coupled to the beam guide and configured to receive ultrasonic information corresponding to portions of the laser beam that have exited the cavity through the plurality of output apertures; and
a meter coupled to the plurality of fiber optic lines and configured to generate data corresponding to the ultrasonic information received by the plurality of fiber optic lines.

16. The system of claim 15, further comprising a processing device configured to receive the data and produce an image corresponding to the data.

17. The system of claim 16, wherein the image comprises a two-dimensional mapping of a surface of an object, a three-dimensional mapping of the surface of the object, or a combination thereof.

18. The system of claim 15, wherein the meter comprises an interferometer.

19. A method of non-destructive testing of an object, comprising:
illuminating the object using an apparatus, wherein the apparatus comprises:
a beam guide comprising an input aperture, a cavity, and a plurality of output apertures, wherein:
the input aperture is coupled with the cavity and configured to receive a laser beam and to direct the laser beam into the cavity; and
the plurality of output apertures is formed in the cavity and spaced apart along the cavity, wherein each output aperture of the plurality of output apertures is configured to direct a portion of the laser beam out of the cavity; and a plurality of fiber optic lines coupled to the beam guide and configured to receive ultrasonic information corresponding to portions of the laser beam that have exited the cavity through the plurality of output apertures;

generating data corresponding to the ultrasonic information received by the plurality of fiber optic lines;

forming a mapping of a surface of the object using the data; and analyzing the mapping of the surface of the object to determine whether the object has a defect.

20. The method of claim 19, wherein the mapping comprises a two-dimensional mapping or a three-dimensional mapping.

* * * * *